United States Patent [19]

Kaper et al.

[11] Patent Number: 4,935,364

[45] Date of Patent: Jun. 19, 1990

[54] **METHOD OF ISOLATING RESTRICTION FRAGMENT DELETIONS IN *VIBRIO CHOLERAE* AND PRODUCTS THEREOF**

[75] Inventors: James B. Kaper; Myron M. Levine, both of Columbia, Md.

[73] Assignee: Swiss Serum and Vaccine Institute Berne, Berne, Switzerland

[21] Appl. No.: 363,383

[22] Filed: Jun. 5, 1989

Related U.S. Application Data

[63] Continuation of Ser. No. 867,633, May 27, 1986, abandoned, which is a continuation of Ser. No. 472,276, Mar. 4, 1983, abandoned.

[51] Int. Cl.$^5$ .................... C12N 15/00; C12N 1/20; C12R 1/63
[52] U.S. Cl. .................. 435/172.3; 435/172.1; 435/252.3; 435/909; 435/320; 935/56; 935/72
[58] Field of Search .............. 435/172.3, 172.1, 252.3, 435/320, 909; 935/56, 72

[56] References Cited

U.S. PATENT DOCUMENTS 4,666,837 5/1987 Harford et al. .................. 435/68

FOREIGN PATENT DOCUMENTS 0018154 10/1980 European Pat. Off. ......... 435/172.2

OTHER PUBLICATIONS

Levine et al., *The Lancet*, Aug. 1988, pp. 467–470.
ASM, Annual Meeting, 1989, Brickman et al., Abstract B-192.
Levine et al., *Infect & Immunity*, vol. 56, No. 1, pp. 161–167, Jan. 1988.
Levine et al., *Infect & Immunity*, vol. 43, No. 2, pp. 515–522, Feb. 1984.
Kaper et al., *Biol. Technology*, vol. 2, pp. 345–349, 1984.
Kaper, James et al., *Nature*, vol. 308, pp. 655–658, Apr. 12, 1984.
Mekalanos, J. et al., *Proc. Natl. Acad. Sci.*, vol. 79, pp. 151–155, 1982.
Pearson, G. D. et al., *Proc. Natl. Acad. Sci.*, vol. 79, pp. 2976–2980, 1982.
Matzke, A. J. et al., *J. Molec. & Applied Genetics*, vol. 1, pp. 39–49, 1981.
Chilton, M. et al., *Stadler Symp.*, vol. 13, pp. 39–52, 1981.
Levine, M. M. et al., *Acute Enteric Infections in Children, New Prospects for Treatment*, (Holme et al., Eds.), pp. 443–459, 1981.
Sutcliffe et al., *Genetic Engineering*, (Chakrabarty, Ed.), pp. 83–100, 1978.
Kaper, J. B. et al., *Infect & Immunity*, vol. 32, pp. 661–667, 1981.
Thomas, J. A. et al., *J. Bacteriology*, vol. 148, pp. 374–378, 1981.
Sublett, R. et al., *Infect & Immunity*, vol. 32, pp. 1132–1138, 1981.
Kaper, J. B. et al., *Nature*, vol. 308, pp. 655–658, Apr. 1984.
Holmgren, J., *Nature*, vol. 292, pp. 413–417 (1981).
Levine, Myron M. et al., *Microbiological Reviews*, vol. 47, pp. 510–550 (1983).

(List continued on next page.)

*Primary Examiner*—Jayme A. Huleatt
*Attorney, Agent, or Firm*—Bradford E. Kile; Kevin M. O'Brien; Ruffin B. Cordell

[57] ABSTRACT

This invention relates to a method of isolating deletion mutants of *Vibrio cholerae*, wherein the deletion is predetermined by digestion with restriction endonucleases of known specificity. The deletions are inserted into the *Vibrio cholerae* chromosome by in vivo recombination betweem a plasmid carrying the desired deletion, with adjacent flanking sequences, and the *Vibrio cholerae* chromosome. The invention includes the isolation and characterization of a new *Vibrio cholerae* strain having a deletion in the tox gene, as defined by Acc I restriction endonuclease sites.

60 Claims, 4 Drawing Sheets

OTHER PUBLICATIONS

Svennerholm, A.-M. et al., Bulletin of the World Health Organization, vol. 62, pp. 909–918 (1984).

A.-M. Svennerholm et al., The Lancet, pp. 305–308 (Feb. 6, 1982).

Black, Robert E., manuscript, "Protective Efficacy in Man of Killed Whole Vibrio Oral Cholera Vaccine With and Without the B Subunit of Cholera Toxin", to be published in Infection and Immunity.

Sigel, S. et al., Infection & Immunity, vol. 32, pp. 474–479, 1981.

Honda, T. et al., Proc. Natl. Acad. Sci., vol. 76, pp. 2052–2056, 1979.

Mekalanos, J. et al., Nature, vol. 306, pp. 551–557, Dec. 1983.

Mekalanos, Cell, vol. 35, pp. 253–263, Nov. 1983.

Kaper, J. et al., Vaccines 85–Molecular and Chemical Basis to Viral, Bacterial and Parasitic Diseases, (Cold Spring Harbor, N.Y.), pp. 107–111, 1985.

Levine, M. et al., Transactions Royal Society of Tropical Medicine and Hygiene, vol. 73, pp. 3–9, 1979.

Curlin, G. et al., Proc. 11th Joint Conf. on Cholera, U.S.-Japan Cooperative Med. Sci. Program, pp. 314–329, 1975.

Noriki, H., Proc. 12th Joint Conf. on Cholera U.S.-Japan Cooperative Med. Sci. Program, pp. 302–310, 1977.

METHOD OF ISOLATING RESTRICTION FRAGMENT DELETIONS IN *VIBRIO CHOLERAE* AND PRODUCTS THEREOF

This is a continuation of Ser. No. 867,633, filed May 27, 1986, now abandoned, which is a continuation of Ser. No. 472,276, filed May 4, 1983, now abandoned.

BACKGROUND OF THE INVENTION

*Vibrio cholerae* (*V. cholerae*) is a non-invasive enteropathogen of the small bowel that does not penetrate the mucosal surface. Local SIgA mediated immunity at the mucosal surface is therefore implicated as a protective mechanism. Pathogenic *V. cholerae* 01 elaborate a protein enterotoxin (also known as cholera enterotoxin, or choleragen, or cholera toxin) which is responsible for induction of copious secretion by the intestine resulting in watery diarrhea, the clinical consequence of cholera infection. Cholera diarrhea can be extraordinarily severe and result in loss of so much body water and salts that dehydration, acidosis, shock, and death ensue without prompt therapy.

The cholera vaccines that have been developed can be broadly divided into two categories; those aiming to stimulate antitoxic immunity and those intending to induce antibacterial immunity. Experiments with animal models support a protective role for either or both antitoxic and antibacterial immunity. It has been suggested that when both types of immunity work in unison, there is a synergistic effect. [Holmgren, J. et al. *J. Infect. Dis.* 136 *Suppl.,* S105–S1122 (1977); Peterson, J. W. *Infect. Immun.* 26, 594 (1979); Resnick, I. G. et al. *Infect. Immun.* 13, 375 (1980; Svennerholm, A.-M. et al. *Infect. Immun.* 13, 735 (1976)]. However, it appears that protective immunity in humans can be conferred without such synergistic effect, that is by either antitoxic immunity or antibacterial immunity [Eubanks, E. R. et al. *Infect. Immun.* 15, 533 (1977); Fujita, K. et al. *J. Infect. Dis.* 125, 647 1972); Holmgren, J., *J. Infect. Dis.,* supra; Lange, S. et al. *Acta Path. Microbiol. Scand. Sect. C* 86, 145 (1978); Peterson, J. W., supra 1979; Pierce, N. F. et al. *Infect. Immun.* 37, 687 (1982); Pierce, N. F. et al. *Infect. Immun.* 21, 185 (1978); Pierce, N. F. et al. *J. Infect. Dis.* 135, 888 1977; Resnick, I. G. et al., supra; Svennerholm, A.-M. et al, supra].

KILLED WHOLE CELL VACCINES

1. Parenteral Whole Cell Vaccines

For almost a century, killed whole *V. cholerae* have been employed as parenteral vaccines; these vaccines are still commercially available. Experience with the parenteral whole cell vaccines has been reviewed recently in Joo, I. "Cholera Vaccines." In *Cholera* (Barua D. and Burrows W., eds.), Saunders, Philadelphia, pp. 333–355 (1974) and in Feeley, J. D. et al. In *Cholera and Related Diarrheas.* 43rd Nobel Symp., Stockholm 1978. (O. Oucherlong, J. Holmgren, eds.) Karger, Basel, pp. 204–210 (1980). Such vaccines stimulate high titers of serum vibroicidal antibodies. They also stimulate increases in intestinal SIgA antibody to *V. cholerae* somatic O antigen when given to Pakistanis but not to Swedes [Svnnerholm, A.-M. et al. *Infect. Immun.* 30, 427 (1980); Svennerholm, A.-M. et al. *Scan. J. Immun.* 6, 1345 (1977)]. It has been suggested that the Pakistani vaccine recipients respond in this way because they are already immunologically primed from prior antigenic contact, while persons living in a non-endemic area (e.g., Sweden) are not. In field trials parenteral killed whole cell vaccines have been shown to confer significant protection against the homologous *V. cholerae* serotype, but usually for a period of less than one year [Joo, I., supra; Feeley, J. C., supra; Svennerholm, A.-M. et al. supra, 1980; Svennerholm, A.-M. et al. supra, 1977; Mosley, W. H. et al. *Bull. Wld. Hlth. Org.* 49, 13 (1973); Philippines Cholera Committee, *Bull. Wld. Hlth. Org.* 49, 381 (1973)]. There is some evidence to suggest that parenteral whole cell Inaba vaccine provides good, short term protection against Ogawa, as well as against Inaba cholera, while Ogawa vaccine is effective only against Ogawa.

By use of adjuvants, it has been possible to maintain a vaccine efficacy of approximately 70% for up to one-and-one-half years with parenteral vaccine (see, e.g., Saroso, J. S. et al. *Bull. Wld. Hlth. Org.* 56, 619 (1978)). However, the adverse reactions encountered at the site of inoculation (which include sterile abscesses) with adjuvanted vaccines are sufficiently frequent and severe to preclude routine use of such adjuvanted vaccines

2. Oral Whole Cell Vaccines

[Freter, R. J. *Infect. Dis.* 111, 37 (1972); Freter, R. et al. *J. Immunol.* 91, 724 (1963); Ganguly, R. et al. *Bull. Wld. Hlth. Org.* 52, 323 (1975)]. Other investigators have shown substantial vaccine efficacy, but' a large proportion of the vaccinees developed diarrhea after subsequent challenge with pathogenic vibrios [Cash, R. A. et al. *J. Infect. Dis.* 130, 325 (1974)].

Toxoids

Immunizing agents intended to prevent cholera by means of stimulating antitoxic immunity include:

(1) Formaldehyde-treated cholera toxoid;
(2) Glutaraldehyde-treated cholera toxoid;
(3) Purified B subunit; and
(4) Procholeragenoid (with or without formaldehyde treatment).

1. Formaldehyde-Treated Cholera Toxoid

Treatment of purified cholera toxin in vitro with formaldehyde eradicates its toxicity, resulting in a toxoid that exhibits little toxic biological activity but stimulates antitoxic antibodies following parenteral immunization of animals. However, when the first toxoid of this type was administered to monkeys and man as a parenteral vaccine, the toxoid reverted to partial toxicity causing unacceptable local adverse reactions at the site of inoculation [Northrup, R. S. et al. *J. Infect. Dis.* 125, 471 (1972)]. An aluminum-adjuvanted formalinized cholera toxoid has been administered parenterally to Bangladeshi volunteers, including lactating mothers, but no field trials with this vaccine have been undertaken [Merson, M. H. et al. *Lancet I,* 931 (1980)]. Formalinized cholera toxoid prepared in the presence of glycine has also been tried by the parenteral route, but the vaccine showed no evidence of efficacy [Ohtomo, N. In *Proceedings of the 12th Joint Conference on Cholera,* U.S.-Japan Cooperative Medical Science Program, Sapporo (Fukumi H., Zinnaka Y., eds.) pp. 286–296 (1976); Noriki, H. In *Procedings of the 12th Joint Conference on Cholera,* U.S.-Japan Cooperative Medical Science Program, Sapporo (Fukumi H., Zinnaka Y., eds.) pp. 302–310 (1976)].

2. Glutaraldehyde-Treated Cholera Toxoid

Methods have been developed for the large-scale preparation of a glutaraldehyde-treated cholera toxoid that is essentially free of contaminating somatic antigen [Rappaport, E. S. et al. *Infect. Immun.* 14, 687 (1976)]. It was hoped that this antigen could be used to assess in a "pure" manner the protective role of antitoxic immunity alone. A large-scale field trial of this toxoid given as a parenteral vaccine was carried out in Bangladesh in 1974 [Curlin, G. et al. In *Proceeding of the 11th Joint Conference on Cholera*, U.S.-Japan Cooperative Medical Science Program. pp. 314–329, New Orleans, (1975)]. The toxoid stimulated high titers of circulating antitoxin in Bangladeshi recipients. Two waves of cholera, El Tor Inaba followed by El Tor Ogawa, struck the field area allowing a fair evaluation of vaccine efficacy. A protective effect could be demonstrated in only one age group and was restricted to the period of the Inaba epidemic, thus, glutaraldehyde-treated cholera toxoid given alone as a parenteral vaccine provided little protection and was substantially inferior to similar field trials in the same population with parenteral killed whole cell vaccines.

The use of glutaraldehyde-treated cholera toxoid as an oral vaccine has been investigated on the assumption that toxoid given by this route might be more efficient by stimulating intestinal antitoxin [Levine, M. M. et al. *Trans. Roy. Soc. Trop. Med. Hyg.* 73, 3 (1979)]. Two groups of volunteers were immunized with three 2.0 mg, or three 8.0 mg doses of toxoid given directly into the small intestinal lumen (via intestinal tube) at monthly intervals. The vaccinees and unimmunized controls then participated in experimental cholera challenge studies. In neither challenge study was the attack rate or severity of diarrhea significantly diminished in the vaccinees when compared with controls The lack of efficacy of oral glutaraldehyde-treated cholera toxoid may be due to the fact that the capacity of B subunits to bind to GM1 ganglioside is greatly diminished as a consequence of toxoiding with glutaraldehyde.

3. Purified B Subunit

Cholera enterotoxin is composed of two subunits designated A and B. The A subunit induces the enzymatic changes which lead to fluid secretion, while the non-toxic B subunit is the immunogenic moiety that binds to the receptor for toxin (GM1 ganglioside) on intestinal epithelial cells [Holmgren, J. *Nature* 292, 413 (1981)]. It has been shown that purified B subunit given either orally or parenterally to Bangladeshis stimulates the appearance of SIgA antitoxin in intestinal fluid, a result attributable to immunological priming in a cholera-endemic area [Svennerholm, A.-M. et al. *Lancet I*, 305 (1982)].

The major advantages of B subunit oral vaccine to stimulate antitoxic immunity include its complete safety (there is no potential for reversion to toxin as exists with toxoids) and retention of its capacity to adhere to toxin receptors on enterocytes. Animal studies suggest that it is less potent than native holotoxin in stimulating antitoxin [Pierce, N. F., supra, (1982)].

It will be understood that the purified B subunit can be used, if at all, in conjunction with (e.g., oral killed) vibrios as a combination oral vaccine intended to stimulate both antibacterial and antitoxic antibodies.

4. Procholeragenoid

Procholeragenoid is the large molecular weight toxoid (ca. 1,000,000 MW) that results when cholera enterotoxin is heated at 65° C. for at least five minutes [Finkelstein, R. A. et al. *J. Immunol.* 107, 1043 (1971)]. It is immunogenic while retaining less than 5% of the biological toxic activity of the parent toxin Heating for longer times (e.g., 25 minutes) produces less biological toxicity [Germanier, R. et al. *Infect. Immunl* 13, 1692 (1976)], and subsequent treatment with formaldehyde completely abolishes residual biological toxicity The resultant formaldehyde-treated procholeragenoid is at least as potent as the parent toxin in stimulating serum antitoxin following immunization of rabbits. Swiss volunteers developed brisk serum antitoxin responses following parenteral immunization with 10, 30, or 100 mcg doses of formaldehyde-treated procholeragenoid [Germanier, R. et al. *J. Infect. Dis.* 135, 512 (1977)]. No notable adverse reactions were observed.

As an oral antigen procholeragenoid is more immunogenic when given in the form without formaldehyde-treatment. In dogs, untreated procholeragenoid is tolerated as well as an oral vaccine; oral doses (with $NaHCO_3$) up to 500 mcg do not cause diarrhea. Five 500 mcg doses spaced over 42 days stimulate significant protection in dogs against oral challenge with pathogenic *V. cholerae*. Doses of 50 mcg and 200 mcg with $NaHCO_3$ have been given to groups of six and four adult volunteers, respectively, without eliciting adverse reactions.

It will be understood that procholeragenoid can be used in conjunction with (e.g., killed) vibrios or other relevant antigens capable of stimulating antibacterial immunity so that the antitoxic immunity induced by procholeragenoid is enhanced.

Combination Vaccines

The major attraction of non-living, oral cholera vaccine is its safety. An oral vaccine consisting of a combination of antigens, intending to stimulate both antibacterial and antitoxic immunity, would be most likely to succeed for the following reasons: Toxoid vaccines that stimulate purely antitoxic immunity have not been shown to be efficacious in protecting man against cholera, although they may protect animal models In addition, oral or parenteral killed whole cell vaccines that stimulate no antitoxic immunity provide significant protection against cholera in man, albeit for a short period of time. Furthermore, combinations of antigens (such as crude cholera toxin, or toxin plus lipopolysaccaride) that stimulate both antitoxic and antibacterial immunity, give synergistic protection.

Two studies so far have been carried out in man with combination vaccines. In the first, nine volunteers who ingested glutaraldehyde-treated cholera toxin (2 mg weekly for four weeks) plus killed El Tor Inaba vibrios ($10^{10}$ vibrios twice weekly for four weeks) were challenged after one month with $10^6$ pathogenic El Tor Inaba vibrios, along with six unimmunized controls Diarrhea occurred in only two of nine vaccinees, versus four of six controls (vaccine efficacy 67%) and illness was clearly attenuated in the two ill vaccinees. More pertinent, perhaps, is the observation that *V. cholerae* could be directly cultured from stools of only two of nine vaccinees, versus six of six controls. This demonstrates that immunologic mechanisms impeded the proliferation of vibrios.

More recently, three doses of B subunit/killed whole cell vaccine was given to adult volunteers who participated in a vaccine efficacy challenge. The combination vaccine was given on days 0, 14, and 28. Each of the three doses of vaccine contained 0.5 mg of purified B subunit and $2 \times 10^{11}$ killed *V. cholerae* ($5 \times 10^{10}$ classical Inaba, $5 \times 10^{10}$ classical Ogawa, and $1 \times 10^{11}$ El Tor Inaba).

A group of eleven volunteers immunized with this combination vaccine were challenged one month after their last dose with $10^6$ pathogenic *V. cholerae* El Tor Inaba, along with seven control volunteers. Diarrhea occurred in seven of seven controls, but in only four of eleven vaccinees ($p=0.01$). The illness in the four vaccinees was definitely milder.

Thus, results of studies with oral toxoid/killed whole cell vaccine combinations demonstrate a measurable degree of efficacy The protective vaccine efficacy, however, is only moderate (55–65%) and multiple doses are required to induce the protection.

Attenuated *V. Cholerae* Vaccines

Both classical and El Tor clinical cholera infections stimulate a high degree of protective immunity for at least three years in North American volunteers [Cash, R. A. et al., supra (1974); Levine, M. M. et al., supra (1979); Levine, M. M. et al. "Volunteers studies in development of vaccines against cholera and enterotoxigenic *Escherichia coli*: a review," in *Acute Enteric Infections in Children: New Prospects for Treatment and Prevention*. (T. Holm, J. Holmgren, M. Merson, and R. Mollby, eds.) Elsevier, Amsterdam, pp. 443–459 (1981); and Levine, M. M. et al. *J. Infect. Dis.* 143, 818 (1981)]. Based on these observations in volunteers, perhaps the most promising approach toward immunologic control of cholera may be with attenuated non-toxigenic *V. cholerae* strains employed as oral vaccines.

1. Naturally-Occurring Strains

Non-toxigenic *V. cholerae* 01 strains isolated from environmental sources in India and Brazil have been evaluated in volunteers as potential vaccine candidates with disappointing results. They either failed to colonize the intestine of man, or did so minimally; vibrocidal antibody responses were meager, and they failed to provide protection in experimental challenge studies [Cash, R. A. et al. *Infect. Immun.* 10, 762 (1974); Levine M. M. et al. *J. Infect. Dis.* 145, 296 (1982)]. Many of these strains appear to lack the toxin gene, as measured by hybridization with a radioactive DNA probe [Kaper, J. B. et al. *Infect. Immun.* 32, 661 (1981)].

2. Mutagenized Attenuated Strains

Classical Inaba 569B has been mutagenized with nitrosoguanidine (NTG) and a hypotoxinogenic mutant isolated [Finkelstien, R. A. et al. *J. Infect. Dis.* 129, 117 (1974); Holmes, R. K. et al. *J. Clin. Invest.* 55, 551 (1975). This mutant strain, M13, was fed to volunteers. Diarrhea did not occur but the strain colonized poorly. Challenge studies demonstrated that some protective efficacy was conferred by immunization with multiple doses [Woodward, E. et al. *Develop Biol. Stand.* 33, 108 (1976)].

El Tor Ogawa 3083 has also been mutagenized [Honda, T. et al. *Proc. Nat. Acad. Sci.* 76, 2052 (1979)]. Brute force selection and analysis of thousands of colonies yielded one that continued to produce the immunogenic B subunit while failing to produce detectable A subunit or holotoxin. The one isolate, Texas Star-SR, fulfilled these criteria. Texas Star-SR produces normal or increased amounts of B subunit but is negative in assays for holotoxin activity or A subunit activity.

Texas Star-SR has been extensively evaluated in volunteers (see, e.g., Levine M. M. et al. *Acute Enteric*, supra (1981)). Groups of five to fourteen volunteers ingested $10^5$ to $5 \times 10^{10}$ Texas Star-SR organisms in a single dose; eight other volunteers received two $10^9$ organism doses one week apart and eighteen more volunteers ingested two $2 \times 10^{10}$ organism doses one week apart. Some degree of diarrhea was seen in sixteen of the sixty-eight vaccinees (24%). In only one individual did the total stool volume exceed 1.0 liter (1464 ml). Typically, the vaccine-induced diarrhea consisted of two or three small, loose stools totaling less than 400 ml in volume. Vaccine organisms were recovered from coprocultures of approximately one-half of the vaccine recipients. Where jejunal fluid was cultured (recipients of doses of $10^8$ or more vaccine organisms), cultures were positive in thirty-five of forty-six vaccinees (76%). Hundreds of Texas Star clones recovered from coprocultures and jejunal fluid cultures were examined for cholera holotoxin by the sensitive Y-1 adrenal cell assay; none were positive.

Significant rises in serum antitoxin were detected in only 29% of the vaccinees; however, 93% manifested significant rises in serum vibriocidal antibody and the titers were substantially close to those encountered following infection with pathogenic *V. cholerae*. In experimental challenge studies in volunteers, Texas Star-SR was found to confer significant protection against challenge with both El Tor Ogawa and El Tor Inaba vibrios. One or two doses of Texas Star-SR attenuated oral vaccine confers good protection against El Tor cholera.

It is clear that the use of attenuated strains has intrinsic advantages since such strains mimic infection-derived immunity to cholera However, the Texas Star-SR strain suffers from certain drawbacks. To begin with, mutagensis (e.g., with nitrosoguanidine) induces multiple mutations, not all of which are necessarily recognized. Furthermore, the precise genetic lesion that is presumed to be responsible for the attenuation of Texas Star-SR is not known. In addition, Texas Star-SR may revert to virulence, like any pathogen mutated with nigrosoguanidine.

Applicants of the present invention have isolated, by novel methods, deletion mutants of a virulent strain of *Vibrio cholerae* known to produce both immunity and disease in volunteers. The deletions are restriction endonuclease fragments. The vaccine strains of the present invention have been specifically altered through the use of recombinant DNA techniques to render them avirulent without affecting other components necessary for immunity. This attenuation was accomplished by using restriction endonucleases which cleave the DNA of the bacterium at specific sites, to specifically delete the genes responsible for cholera toxin (i.e., the tox gene). Plasmids carrying the tox gene were digested with restriction endonucleases to delete the tox gene, but were constructed to retain extensive lengths of flanking DNA of the *V. cholerae* chromosome. Conjugal gene transfer of these plasmids into *V. cholerae* yielded a virulent *V. cholorae* strain carrying extrachromosomal copies of the plasmids. Subsequent conjugation with cells having other plasmids produced, after appropriate selection of selectable plasmid markers, *V. cholerae* strains having deletions in the tox regions. Such nontoxigenic deletion mutants would then be capable of colonizing the small intestine and stimulating local, protective immunity directed against the bacterial cell. After the transient colonization episode, the vaccine would be protective against subsequent infection with virulent toxigenic *V. cholerae* strains.

The genes for *V. cholerae* toxin have been cloned [Pearson, G. D. N. et al. *Proc. Nat. Acad. Sci.* 79, 2976 (1982); Kaper, J. B. et al. *Amer. Soc. Microbiol. Abstr. Annu. Meeting, Atlanta, Georgia,* 36 (1982); Kaper, J. B. et al. *Symposium on Enteric Infections in Man and in Animals: Standardization of Immunological Procedures,* Dublin, Ireland, Abstract No. 2.5 (1982)]. Toxin structural gene deletion mutants of *V. cholerae* have been isolated, but by infection with mutagenic vibriophages capable of integration at random sites along the chromosome [Mekalanos, J. J. et at *Proc. Nat. Acad. Sci.* 79, 151 (1982)]. Recombination in *Vibrio cholerae* has been reported, but it has not been used to isolate restriction fragment deletions in the tox genes for vaccination purposes [Parker, C. et al. *J. Bact.* 112, 707 (1972); Johnson, S. R. et al. *Molec. Gen. Genet.* 170, 93 (1979); Sublett, R. D. et al. *Infect. Immun.* 32, 1132 (1981); and Thomson, J. A. et al. *J. Bact.* 148, 374 (1981)].

BRIEF DESCRIPTION OF THE INVENTION

A culture of *Vibrio cholerae* is described comprising a *Vibrio cholerae* strain having a restriction endonuclease fragment of DNA deleted to confer avirulence and to retain capacity to colonize the intestine of a host animal. One isolated deletion mutant encompasses a deletion in the tox gene, as defined by Acc I restriction endonuclease sites.

A method of isolating such deletion mutants of *Vibrio cholerae* is also described, comprising the steps of (a) constructing a first plasmid comprising *Vibrio cholerae* flanking sequences of one or more deleted restriction endonuclease fragments and a gene for a first selectable marker of foreign origin ligated to said flanking sequences to substitute for and to be in the place of said deleted fragment, wherein said sequences are of sufficient length to promote detectable in vivo recombination; and (b) mating a virulent strain of *Vibrio cholerae* with a first microorganism carrying the first plasmid; and (c) selecting for *Vibrio cholerae* expressing the first selectable marker; and (d) mating the selected product of step (c) with a second microorganisim carrying a second plasmid with a second selectable marker, said second plasmid being incompatible with the first plasmid; and (e) selecting for *Vibrio cholerae* expressing both the first selectable marker and the second selectable marker.

The *Vibrio cholerae* deletion mutants of this invention are useful in vaccination against cholera.

BRIEF DESCRIPTION OF THE DRAWINGS

Abbreviations for restriction endonuclease sites in the drawings are as follows.

A=Acc I restriction endonuclease site
B=Bgl II restriction endonuclease site
E=Eco RI restriction endonuclease site
H=Hind III restriction enconuclease site
P=Pst I restriction endonuclease site
S=Sal I restriction enconuclease site Other abbreviations in the drawings include.

Ap=Ampicillin resistance gene
Ap$^r$=Ampicillin resistance phenotype
Ap$^s$=Ampicillin sensitive phenotype
Chrom=Chromosome
Cm=Chloramphenicol resistance gene
CTB=gene for B subunit of cholera toxin
Su=Sulfonamide
Su$^r$=Sulfonamide resistance phenotype
Tp=Trimethoprin

DETAILED DESCRIPTION OF THE INVENTION

The principle of the present invention is the isolation of a *Vibrio cholerae* vaccine strain specifically altered through recombinant DNA technology to render it avirulent without affecting other components necessary for immunity. This attenuation was accomplished by restriction endonuclease digestion of plasmids carrying appropriate *V. cholera* sequences, to specifically delete the genes coding for cholera toxin. Conjugal gene transfer of these digested plasmids, followed by procedures for selecting in vivo recombinants with virulent host *V. cholera,* resulted in strains without the toxin genes. It will be understood that the methods of the present invention are applicable to the isolation of other deletion mutants of virulent *V. cholerae,* or to the isolation of strains having all or part of such deleted sequences reintroduced into the *V. cholerae* cell.

The starting material for the vaccine was the toxigenic *Vibrio cholerae* strain N16961, which has been demonstrated to produce in volunteers both typical diarrheal disease and strong, protective immunity to subsequent infection [Levine, M. M. et al., *Acute enteric,* supra, 1981]. The region of the bacterial chromosome which was found to be responsible for production of cholera toxin was cloned into the plasmid cloning vehicle pBR325, after screening Hind III digests of *V. cholerae* with an *E. coli* heat-labile enterotoxin gene probe [Kaper et al. *Amer. Soc.,* supra; Kaper et al. *Symposium,* supra]. The *V. cholerae* chromosome fragment was found to contain all genes necessary for toxin production. Next, this chromosomal region was then analyzed and mapped for the exact portions containing the toxin genes [Kaper, J. B. et al. *Lancet II,* 1162 (1981)]. Restriction enzymes were employed to cut out the DNA fragments containing these genes and a DNA fragment encoding a selectable marker (e.g., resistance to ampicillin) was inserted by ligation. The ampicillin resistance gene and the flanking Vibrio DNA were then cloned in a derivative of pRK290 which can be transferred from *E. coli* to *V. cholerae.* The resulting plasmid, pJBK55, was transferred from *E. coli* K-12 to *V. cholerae* N16961 by conjugation.

Figure 1:
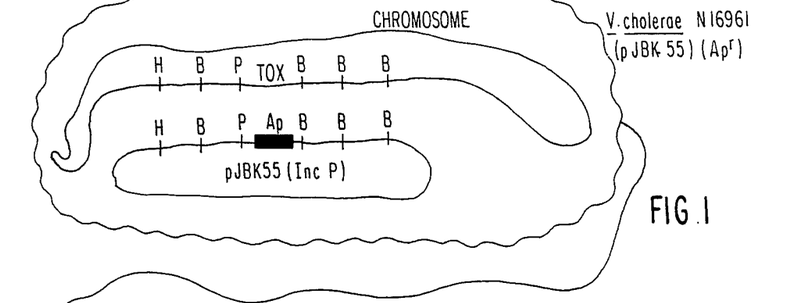
FIG. 1. *V. cholerae* N16961 (pJBK55)(Ap$^r$).
Figure 2:
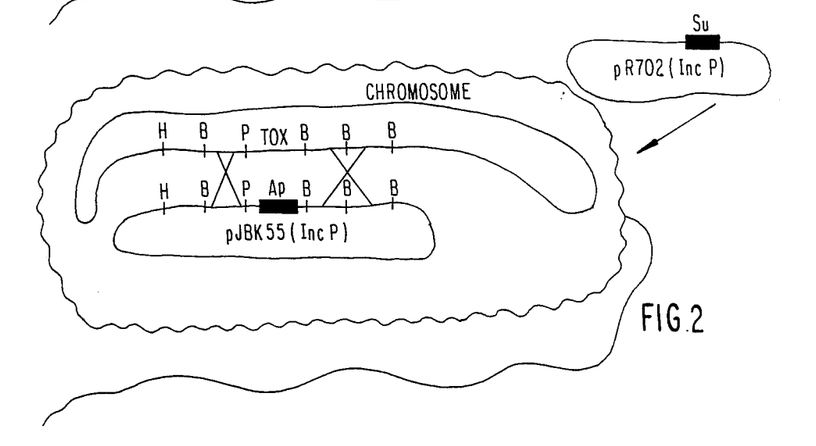
FIG. 2. Processes of crossing-over and conjugal gene transfer to construct *V. cholerae* JBK 56.
Figure 3:
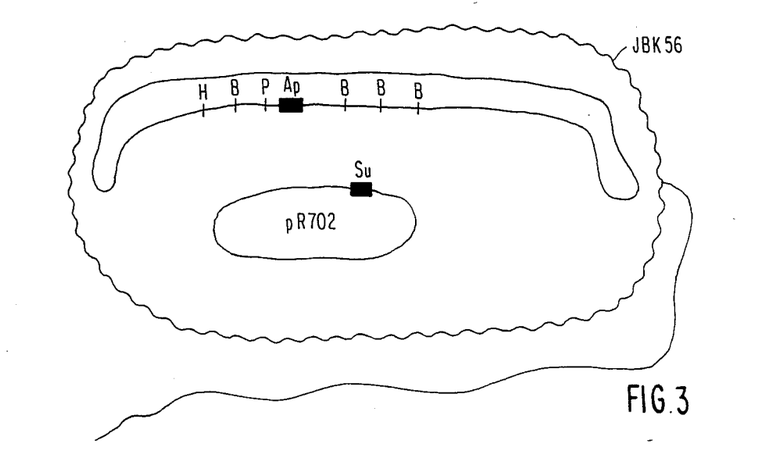
FIG. 3. *V. cholerae* JBK 56.

The resulting strain, *V. cholerae* N16961 (pJBK55) (Ap$^r$) contained a region in its chromosome having intact toxin genes and, in an extrachromosomal state, a plasmid containing this same region with the toxin genes deleted and a gene for ampicillin substituted (See FIG. 1.) At a low frequency, perhaps one in $10^6$ to one in $10^8$, the identical regions flanking the chromosomal toxin genes and the extrachromosomal (plasmid) ampicillin resistance gene will exchange and "cross over" or undergo in vivo recombination so that the region of DNA containing the resistance gene displaces the toxin gene on the chromosome (FIG. 2). This rare mutation is selected by testing a mixture of mutated and non-mutated cells for individual cells which are able to serve as host for an incoming incompatible plasmid [Ruvkun, G. B. et al Nature 289, 85 (1981)]. Plasmids are divided into groups designated A through W, the members of which cannot stably coexist with each other. For example, a plasmid of incompatibility group P cannot be stably maintained in the same cell as another P group (Inc P) plasmid. Thus, Inc P plasmids, such as R702, which specify resistance to sulfonamide, cannot be maintained in a cell which has another Inc P plasmid such as PRK290, pJBK45, or pJBK55. Therefore, R702 can be maintained in a strain in which the ampicillin resistance has recombined into the chromosome but not one in which an Inc P plasmid (e.g., pJBK55) is replicating extrachromosomally. By mating an E. coli strain containing Inc P R702 (sulfonamide resistant) and V. cholorae pJBK55 (ampicillin resistant) and selecting for V. cholerae which are resistant to both ampicillin and sulfonamide, colonies are isolated in which the sulfonamide resistance is mediated extrachromosomally by pR702 and the ampicillin resistance is mediated chromosomally through substitution of the ampicillin resistance gene for the toxin gene (FIG. 3). One such strain, designated V. cholerae JBK56 was isolated and when tested for toxin production was found to be nontoxinogenic.

The final version of the vaccine strain JBK70, was produced by substituting resistance to ampicillin, a therapeutically useful antibiotic, with resistance to mercury. This substitution was accomplished by cloning a gene for mercury resistance directly into the ampicillin resistant gene of pJBK55, thereby inactivating ampicillin resistance and conferring mercury resistance. The resulting plasmid, pJBK66 was also incompatible with R702 and was transferred to V. cholerae JBK56. A mutant in which the mercury resistance was recombined into the chromosome was selected using the Inc P plasmid R702 and selecting for V. cholerae which were ampicillin sensitive, mercury resistant, and sulfonamide resistant. A spontaneous derivative was later selected which was cured of pR702. The final mutant, JBK70, was nontoxinogenic and resistant to mercury only.

The vaccine strain V. cholerae JBK70 is one of the Inaba serotype. The other major serotype of V. cholerae is the Ogawa serotype. It is expected that a vaccine prepared from one serotype will protect against the other serotype (34). In the event that this is not the case, a live vaccine strain was prepared from an Ogawa serotype strain, E7946, previously shown to produce both disease and protection in volunteers [Levine, M.M. et al Acute enteric, supra (1981)]. The exact mutation created in strain V. cholerae Inaba JBK56 was recreated in strain E7946 by directly transferring the region of the chromosome containing the ampicillian resistance in place of the toxin gene in JBK56 into E7946 through genetic recombination mediated by P, the sex factor of V. cholerae [Parker, C. et al., supra]. The P factor, which is distinct from Inc P plasmids, was transferred into JBK56 and was then mated with a rifampin resistant mutant of E7946. By selection of a mutant which was resistant to both ampicillian and rifampin, a vaccine strain was isolated which was of the Ogawa serotype with the toxin genes completely deleted.

If antibacterial immunity is insufficient for protection, then an antitoxic component can be added by adding back the genes for production of cholera toxin B but not A subunit. This has been accomplished by cloning the B subunit gene into the cloning vector pMS9. The resulting plasmid, pJBK51, produces high levels of B subunit and was reintroduced into the nontoxic vaccine strain V. cholerae JBK70 to make an attenuated vaccine strain JBK70(pJBK51) which fails to produce the A subunit.

The vaccine strains of the present invention are derived from V. cholerae N16961 having the serotype Inaba. It will be understood that other strains or other biotypes and serotypes can be used to substitute for N16961 to produce vaccine strains having specific deletions in the tox gene or genes, or in other locations along the V. cholerae chromosome. Since the object of isolating such vaccine strains is to mimic the infection process without associated pathological phenomena, site-directed mutagenesis of virulent strains, as described in this application, produces substantial possibilities in the prophylactic vaccination against cholera.

Production of vaccine strains can be performed by a variety of methods, including the following: Vibrio cholerae is subcultured from stock cultures into brain/heart infusion agar (BHIA) and grown at 37° C. overnight. Identity is tested with group- and type-specific antisera and twenty to thirty colonies are suspended in BHI broth. Preincubated BHIA plates are inoculated with BHI suspension. After incubation for five to six hours, each plate is harvested with 5 ml of sterile saline buffered to pH 7.2±0.1. Harvested organisms are centrifuged in the cold at 750 g for ten minutes, resuspended and washed twice in four-times the original volume. The suspension is standardized spectrophotometrically and diluted to approximate the number of organisms required for vaccination (ca $10^6$, which varies depending on the results of volunteer studies). Replicate, pour-plate quantitative cultures are made of the inocula before and after challenge to confirm inoculum size. The final inoculum is examined with Gram's stain and agglutinated with homologous antiserum prior to feeding.

The Vibrio cholerae strains of the present invention can be administered by the oral route. Two grams of $NaHCO_3$ are dissolved in five ounces of distilled water. Volunteers drink four ounces of the $NaHCO_3$/water; one minute later the volunteers ingest the vibrios suspended in the remaining one ounce of $NaHCO_3$/water. Volunteers are NPO ninety minutes pre- and postinoculation.

With regard to safety, the major concern is that the vaccine strain does not revert to toxigenicity (i.e., produce intact cholera toxin) which could cause disease. The two major assays for testing toxin are the Y-1 adrenal cell assay [Sack, D. A. et al Infect. Immun. 11, 334 (1975)] and the enzyme-linked immunosorbent assay (ELISA) [Sack, D. A. et al J. Clin. Micro. 11, 35 (1980)]. The vaccine strain (JBK70) has been repeatedly tested in these two assays and found to be negative each time. Far more important, however, are the genetic assays performed for the presence of toxin genes. The DNA for cholera toxin genes can be radioactively labeled and used as a specific probe to identify other cholera toxin genes in the strain, according to the method of Southern, E. M. *J. Mol. Bio.* 98, 503 (1975). When tested by this method, the vaccine strain described in the invention possesses no detectable genetic material that can encode cholera toxin. The vaccine has also been tested in an infant mouse model, according to Baselski, V. et al. *Infect. Immun.* 15, 704 (1977). After repeated (ten in all) serial passages, no fluid accumulation (i.e., evidence of disease) has been found. As expected, JBK70 was found to colonize the infant mouse intestine.

In the examples that follow, many of the techniques, reactions, and separation procedures are already well known in the art. All enzymes, unless otherwise stated, are available from one or more commercial sources, such as New England BioLabs—Beverly, Mass.; Collaborative Research—Waltham, Mass.; Miles Laboratories—Elkhart, Ind.; Boehringer Biochemicals Inc.—Indianapolis, Ind.; and Bethesda Research Laboratory—Rockville, Md., to mention a representative few. Buffers and reaction conditions for restriction of enzyme digestion are used according to recommendations supplied by the manufacturer for each enzyme, unless indicated otherwise. Partial digestions with restriction enzymes are carried out using a reduced enzyme concentration which must be predetermined from preliminary experiments for each enzyme batch. Standard methodology for other enzyme reactions, gel electrophoresis separations, and *E. coli* transformation may be found in *Methods in Enzymology,* Volume 68, Ray Wu, editor, Academic Press (1979). Bacteria were grown according to procedures generally described in Miller, *Experiments in Molecular Genetics,* Cold Spring Harbor Laboratory (1972). *Vibrio cholerae* were propagated according to procedures generally described in Lennett, E. A. et al, eds., *Manual of Clinical Microbiology* 3rd Edition, American Society of Microbiology, Washington (1980). *E. coli* and *V. cholerae* were mated according to procedures generally described in Johnson, Steven R. et al. *J. Bact.* 137, 531 (1979); and Yokata, T. et al. *J. Bact.* 109, 440 (1972).

The strains of this invention have been deposited at the American Type Culture Collection, located in Rockville, Md., prior to execution of the present application. The strains deposited are *V. cholerae* JBK56, *V. cholerae* JBK70, *V. cholerae* N16961, *V. cholerae* JBK70-(pJBK51), which have ATCC accession numbers ATCC 39317, ATCC 39318, ATCC 39315, and ATCC 39316, respectively.

EXAMPLE 1

Figure 4:
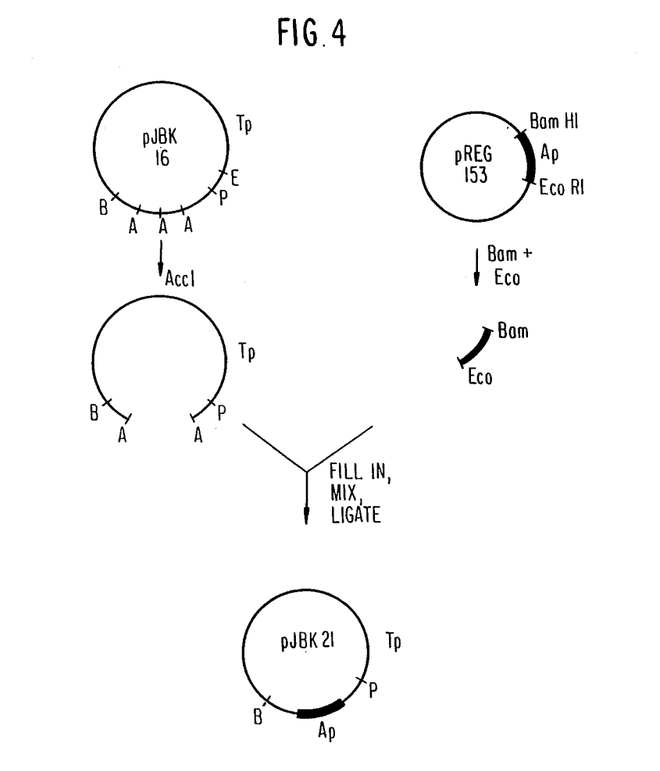
FIG. 4. Scheme for construction of JBK21.

Construction of a Plasmid Having a Selectable Marker Gene Inserted to Replace the Toxin Genes The plasmid JBK16 contains a 4 kb PstI-Bgl II fragment of the chromosome containing the toxin genes. The toxin genes are flanked by Acc I sites and contain an internal Acc I site. JBK16 was digested to completion with Acc I and the Acc I fragments containing the toxin genes were separated from the rest of the plasmid. The remaining overlapping or "sticky" Acc I ends were made blunt-ended by "filling in" with the Klenow fragment of *E. coli.* polymerase (i.e., the single-stranded DNA remaining after Acc I digestion were made double-stranded with flush ends). A gene encoding ampicillin resistance was purified from the plasmid pREG153 (pREG153 is a derivative of pREG151 [Weiss, A. et al. *J. Bact.* 152, 549–552] altered by substitution of ampicillin resistance for trimethoprin resistance and addition of λ cos sequences) and the "sticky" ends "filled in" as above. This fragment was then ligated to the vibrio DNA so that the Ap resistance genes were in exactly the same place as the now-deleted toxin genes, flanked by the same vibrio sequences. The resulting plasmid was designated pJBK21 (FIG. 4) containing the deletion toxin region and the Ap resistance gene.

EXAMPLE 2

Addition of Flanking Homogeneous Sequences, Followed by Conjugal Gene Transfer into *V. cholerae*

Figure 5:
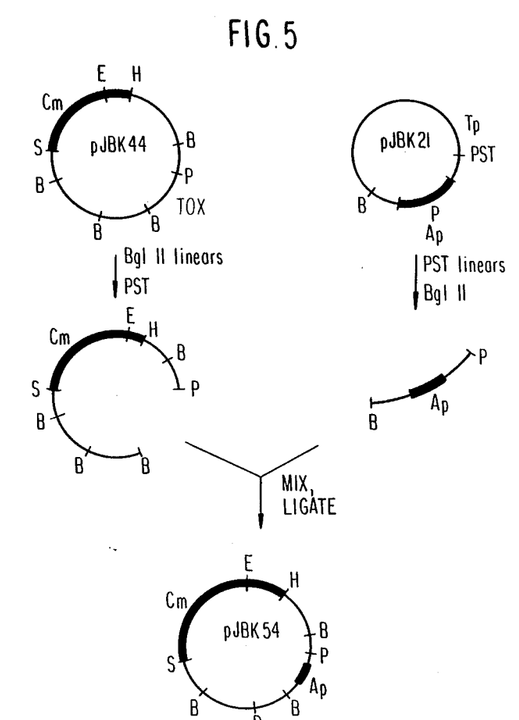
FIG. 5. Scheme for construction of pJBK54.

To insure the specific insertion into the chromosome of the deletion in pJBK21, approximately 7,000 bp of additional DNA was added to each end of the Pst-Bgl II fragment from pJBK21. (The probability of the homologous recombination event occurring increases with increasing length of flanking homologous sequences.) To achieve this, an approximately 18 kb fragment was cloned from the chromosome of N16961. This clone was designated pJBK44 and contains the 4 kb Pst-Bgl tox gene fragment flanked by approximately 7 kb of DNA on each side (see FIG. 5). The plasmid pJBK21 was partially digested with Pst I so that only one of the Pst sites would be cut (an additional Pst site was added within the ampicillin resistance gene) followed by digestion with Bgl II to isolate the 4 kb Pst-Bgl II fragment containing the deletion toxin region and the Ap resistance. The plasmid pJBK44 containing the ca 18 kb vibrio fragment was partially digested with Bgl II so that only one of the 4 Bgl II sites present would be cut. This partial digestion was followed by complete digestion with Pst I and the resulting fragments separated by electrophoresis through 0.3% agarose. The separated fragments were then purified and analyzed and one fragment was found which contained all of the sequences of pJBK44 except for the 4 kb, Pst-Bgl tox gene fragment (see FIG. 5). This fragment representing the flanking DNA was then mixed and ligated to the Pst-Bgl fragment from pJBK21 containing the ampicillin resistance. The resulting plasmid, pJBK54, contained approximately 17 kb of Vibrio chromosome with an ampicillin resistance gene substituted for the deleted toxin genes.

Figure 6:
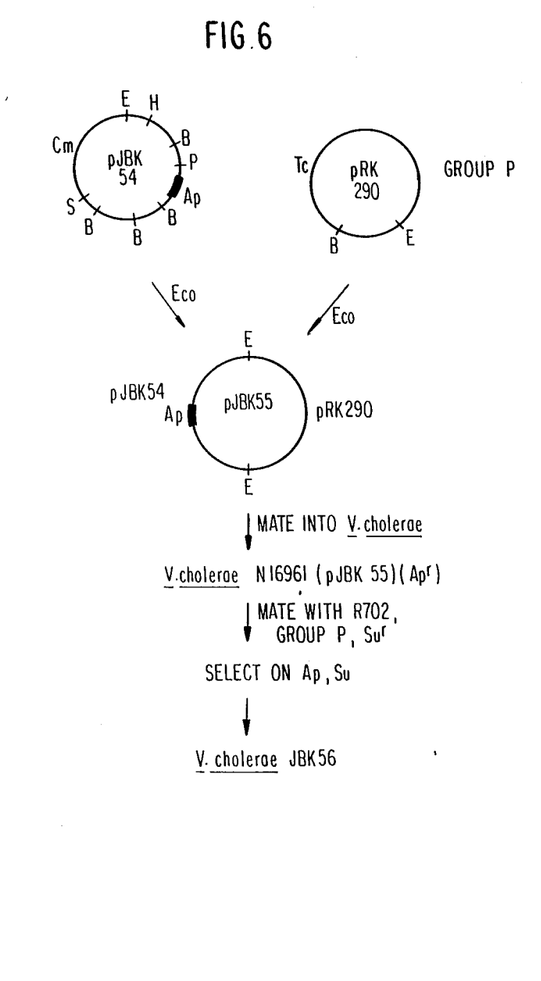
FIG. 6. Scheme for construction of *V. cholerae* JBK56.

The modified chromosomal region was then cloned into a plasmid which can be readily mobilized into *V. cholerae.* The plasmid pRK290 belongs to the plasmid incompatibility group P and possesses a single Eco RI site into which pJBK54 was cloned (FIG. 6). The resulting plasmid pJBK55 was then mated into *V. cholerae* N16961 using the conjugative plasmid pRK2013, yielding *V. cholerae* N16961 (pJBK55)(Ap').

EXAMPLE 3

Recombination in vivo

Figure 7:
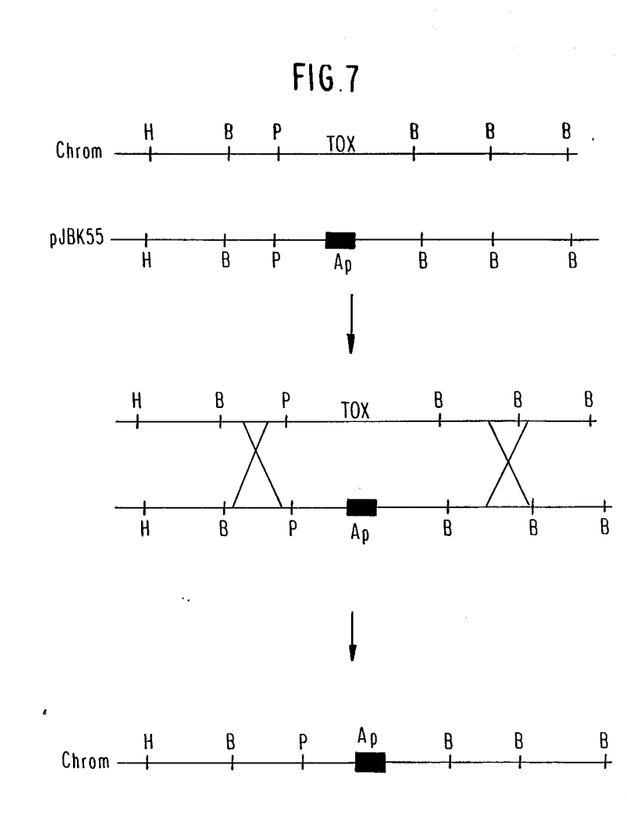
FIG. 7. Recombination in vivo by cross over and elimination of tox gene.

The mutant toxin genes, after conjugal gene transfer as described in Example 3, now existed extrachromosomally in *V. cholerae* strain N169691 (see FIG. 1). At a very low frequency (perhaps $10^{-6}$ to $10^{-8}$) the homologous flanking sequences base pair and cross over into the chromosome (see FIG. 7). This rare event will result in the substitution of the deleted toxin region on the plasmid for the tox genes on the chromosome. To select for this rare event, the plasmid incompatibility phenomenon was exploited [Ruvkin, G. B., supra]. Plasmids can be divided into incompatibility groups, designated A through W, on the basis of their ability to be stably maintained together in the same cell. If two plasmids cannot be stably maintained together in the same cell, they are incompatible and belong to the same incompatibility group, presumably because they utilize the same replication mechanism in the cell. By selectively using an antibiotic resistance present on one plasmid but not on the other, it is possible to select which of two incompatible plasmids will be maintained. The plasmid pJBK55, because of its pRK290 origin, belongs to incompatibility (Inc) group P. The plasmid R702 also belongs to the Inc P group and encodes resistance to kanamycin, tetracycline, sulfonamide, and streptomycin, but not ampicillin. By mating pR702 ($Su^R$) into N16961(pJBK55)($Ap^R$) and selecting on media containing both ampicillin and sulfonamide, selection was made for cells in which the ampicillin resistance had been incorporated into the chromosome and sulfonamide resistance remains on the plasmid R702, since pR702 and pJBK55 are incompatible (see FIG. 2). The resultant strain JBK56 (FIG. 3) was ampicillin resistant, and toxin negative when tested in Y-1 adrenal cells and by $Gm_1$ ELISA. Furthermore, when chromosomal DNA was hybridized to DNA probes containing cloned cholera toxin (CT) genes, JBK56 was negative, suggesting that the toxin genes were completely deleted.

The antibiotic resistance encoded on R702 was eliminated by selecting a spontaneously cured derivative lacking the plasmid (this occurred at a frequency of about 1 in 2,000).

EXAMPLE 4

Elimination of the Selectable Marker of Example 1

To eliminate the ampicillin resistance, a derivative of pJBK55 was constructed in which genes encoding resistance to mercury (Hg) from R100 were cloned into the Pst site of the Ap gene, thereby insertionally inactivating the ampicillin resistance. This derivative was then mated into *V. cholerae* JBK56, followed by pR702 and selection made as above for $Hg^R$, $Ap^S$ *V. cholerae*. The final strain, *V. cholerae* JBK70, is sensitive to all antibiotics tested, resistant to mercury, and phenotypically toxin negative. Its chromosonal DNA did not detectably hybridize to DNA probes containing CT genes. Short of sequencing the DNA for the entire chromosome, JBK70 appears to be unaltered from the parent strain N16961 except for the deletion of the toxin genes and insertion of mercury resistance and inactive ampicillin resistance genes. Such a strain cannot revert to toxigenicity because the toxin genes are not merely mutated but are completely deleted.

EXAMPLE 5

Conjugal Gene Transfer to Confer Antitoxic Immunity

Figure 8:
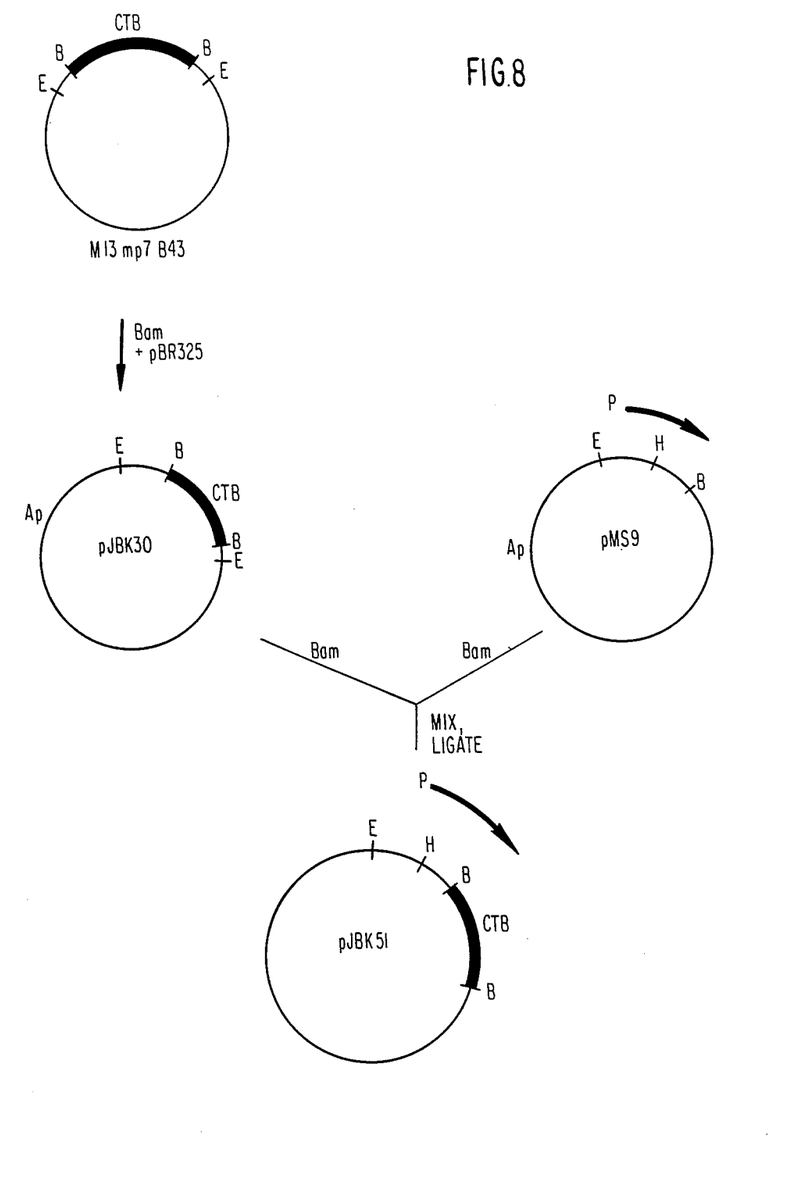
FIG. 8. Scheme for construction of pJBK51.

If both antibacterial immunity and antitoxic immunity are desired for synergy, a derivative of JBK70 can be made to produce the B subunit of cholera toxin only. To accomplish this end, a toxin derivative was made that produces B only and lacks the genes for A (FIG. 8). A Hpa II fragment from pJBK16 containing the B structural gene was cloned into a phage cloning vector, M13mp7 placing a Bam HI and an Eco RI site on either side of the gene (FIG. 8). The fragment, now flanked by Bam HI sites was cloned into pMS 9 which contains the very strong trp promoter. The placing of the B genes under the transcriptional control of a strong promoter insures high production of B antigen. Of the clones examined, approximately 50% produced no antigen. This finding reflects the two possible orientations for the cloned insert—one forward, one backward. One derivative, pJBK51, which produced B subunit was mated into *V. cholerae* JBK70 and found to produce even more B antigen than the parent strain N16961, yielding JBK70(pJBK51). Other B-only mutants have been created using different promoters, including the λ $P_L$ promoter and these can be evaluated in appropriate models for any significant in vivo expression differences.

EXAMPLE 6

Colonization of Infant Mouse Intestiae with JBK70 without Reversion to Toxigenicity Suckling mice (2.0–3.5 g.) were removed from their mothers and starved for 3 to 8 hours. Four of them were then inoculated on day 1 per os to stomach using a 22 g animal feeding needle. The inoculum was about $10^8$ CFU (colony-forming units)/mouse of JBK70 in a volume of between 0.05 ml and 0.1 ml. The inoculum was prepared in BHI broth essentially as described in Baselski, V. et al, supra. The inoculum contained about 0.01% Evans blue dye. The presence of this dye in the stomach, seen through the abdominal wall, indicated proper delivery of the inoculum. Addition of Evans blue dye was discontinued after day 1 (see Table I), to avoid inhibition of JBK70.

Subsequent inoculations involved mouse-to-mouse (MXM), or alternatively, mouse-to-plate-to-mouse (MXPXM), but required different procedures to prepare the inoculum compared to the Baselski protocol for the inoculation on day 1.

To prepare MXM inoculum, the gut was dissected from stomach to anus under sterile precautions. The gut was weighed, placed in a glass homogenizer tube, and about 0.5 ml BHI broth added. The mixture was homogenized briefly with a Teflon pestle until tissue was liquified. The resulting suspension was used to inoculate about $10^8$ CFU into each infant mouse. It was checked for purity by streaking on MEA (meat extract agar) plates. No Evans blue dye was added.

To prepare MXPXM inoculum, a sterile loop was used to transfer cells from an MEA plate to BHI broth. About $10^{11}$ CFU/ml were added to about 1 ml of BHI so that a dense suspension was formed.

TABLE I

| | MOUSE PASSAGE HISTORY OF JBK70 (24 HOUR SCHEDULE) | | | | | | | |
|---|---|---|---|---|---|---|---|---|
| DAY | MXM | D/T | FA RATIO | SHAM D/T | MXPXM | D/T | FA RATIO | COMMENTS |
| 1 | | | | | | | | at 6 p.m. inoc. 4 mice with $10^8$–$10^4$ CFU JBK70 from 24 h plate (Evans Blue Dye was used) |
| 2 noon | MX1 | 2/4 | 0.038 (avg of 2) | | | | | |
| 3 | MX2 | ¼ | 0.051 | | | | | |

TABLE I-continued

MOUSE PASSAGE HISTORY OF JBK70
(24 HOUR SCHEDULE)

| DAY | MXM | D/T | FA RATIO | SHAM D/T | MXPXM | D/T | FA RATIO | COMMENTS |
|---|---|---|---|---|---|---|---|---|
| noon | | | 0.049 | | | | | |
| | | | 0.043 | | | | | |
| 4 noon | MX3 | ⅜ | 0.050 | | MXPXM 1 | ⅜ | 0.040 | |
| 5 1 P.M. | MX4 | 0/5 | 0.043 | 0/5 | | | | |
| | | | 0.044 | | | | | |
| | | | 0.052 | | | | | |
| 6 1 P.M. | MX5 | ⅛ | 0.053 | | | | | |
| | | | 0.064 | | MXPX 2 | 0/3 | 0.060 | |
| | | | 0.053 | | | | 0.054 | |
| 7 3 P.M. | MX6 | ⅛ | 0.063 | | | | | |
| | | | 0.042 | | | | | |
| 8 3 P.M. | MX7 | ⅛ | 0.049 | | MXPXM 3 | 0/3 | 0.045 | |
| | | | 0.050 | | | | 0.051 | |
| | | | | | | | 0.059 | |
| 9 | MXM 8 | ⅜ | 0.054 | | | | | |
| 10 | MXM 9 | 0/3 | 0.041 | | MXPXM 4 | ⅛ | 0.048 | |
| | | | 0.050 | | | | 0.044 | |
| | | | 0.032 | | | | | |
| 11 = | MXM 10 | 0/3 | 0.050 | | | | | |
| | | | 0.054 | | | | | |
| | | | 0.055 | | | | | |
| 12 | MXM 11 | ⅜ | 0.037 | 0/2 | MXPXM 5 | ⅛ | 0.049 | |
| | | | | | | | 0.048 | |

MXM = Passage from Mouse to Mouse
D/T = Deat Total
FA Ratio = weight of gut/(weight of carcass-gut)
MXPXM = Passage from Mouse to Plate to Mouse
SHAM animals were given sterile BHI broth.

The mixture was vortexed to homogeneity, and 0.05–0.1 m. (about $10^{10}$ CFU) inoculated per os into each infant mouse. No evans blue dye was added.

For all inoculations, mice were held in beakers at room temperature of 73°–76° F. Beakers were placed in a plastic box which was loosely covered in order to maintain the mice at slightly above ambient temperature, about 78° F.

As the results in Table I indicate, there were sufficient cells in the intestine to inoculate the next animal, as checked by streaking on MEA plates. The *Vibrio cholerae* JBK70 therefore colonized the gut of infant mice. Furthermore, the fluid accumulation levels did not increase since there were no substantial increases in the FA ration (an FA ratio greater than or equal to 0.065 is a positive fluid accumulation). Evidence of reversion to toxigenicity would have indicated otherwise.

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A culture of *Vibrio cholerae* comprising a *Vibrio cholerae* strain having a restriction endonuclease fragment of DNA coding for *Vibrio cholerae* toxin or the A subunit thereof deleted to confer avirulence and having the capacity to colonize the intestine of a host animal, said strain constructed by selection of an in vivo recombinant between a virulent *Vibrio chloerae* and a first plasmid, said first plasmid comprising *Vibrio cholerae* flanking sequences of the deleted DNA and a gene for a first selectable marker of foreign origin ligated to said flanking sequences to substitute for and to be in the place of said deleted DNA, said flanking sequences being of sufficient length to promote detectable in vivo recombination, said gene for said first selectable marker being incorporated into the chromosome of *Vibrio cholerae*, said selection being performed by selecting for said first selectable marker and for a second selectable marker to isolate an in vivo recombinant in the presence of a second plasmid carrying the second selectable marker, said second plasmid being incompatible with the first plasmid.

2. The culture of *Vibrio cholerae* according to claim 1 wherein said sequences that flank the deleted DNA are about 7,000 base pairs on each side.

3. The culture of *Vibrio cholerae* according to claim 1 wherein said first selectable marker and said second selectable marker are resistance genes.

4. The culture of *Vibrio cholerae* according to any of claim 1, 2 or 3 wherein said first plasmid is pJBK55.

5. The culture of *Vibrio cholerae* according to any of claims 1, 2 or 3 wherein said second plasmid is PR702.

6. The culture of *Vibrio cholerae* according to any of claims 1, 2 or 3 wherein the first selectable marker of the in vivo recombinant is inactivated by insertion of a third selectable marker to yield a final strain of *Vibrio cholerae*.

7. The culture of *Vibrio cholerae* according to claim 6 wherein said final strain carries a plasmid expressing the B subunit of cholera toxin.

8. The culture of *Vibrio cholerae* according to claim 1 wherein said first plasmid is prepared by digesting plasmid JBK 16 with ACC I restriction endonuclease, separating the ACC I fragments from the plasmid, ligating a gene for ampicillin resistance to the remaining DNA so that the ampicillin resistance gene is in the same location that the deleted toxin genes previously occupied, adding about 7,000 base pairs to each side of DNA sequences which flank the ampicillin resistance gene and cloning the resultant DNA into plasmid pRK 290 to form plasmid p JBK 55.

9. The culture of *Vibrio cholerae* according to claim 8 wherein said resultant DNA is cloned into an Eco RI site in said plasmid pRK290.

10. The culture of *Vibrio cholerae* according to claim 1 wherein said deleted DNA codes for the A subunit of *Vibrio cholerae* toxin to confer avirulence.

11. A method of isolating deletion mutants of *Vibrio cholerae* comprising the steps of
   (a) constructing a first plasmid comprising *Vibrio cholerae* flanking sequences of a deleted restriction endonuclease fragment and a gene for a first selectable marker of foreign origin ligated to said flanking sequences to substitute for and to be in the place of said deleted fragment, wherein said flanking sequences are of sufficient length to promote detectable in vivo recombination; and
   (b) mating a virulent strain of *Vibrio cholerae* with a first microorganism carrying the first plasmid; and
   (c) selecting for *Vibrio cholerae* expressing the first selectable marker; and
   (d) mating the selected product of step (c) with a second microorganism carrying a second plasmid with a second selectable marker, said second plasmid being incompatible with the first plasmid; and
   (e) selecting for *Vibrio cholerae* expressing both the first selectable marker and the second selectable marker to isolate an in vivo recombinant.

12. A method according to claim 11 further comprising the steps of
   (f) mating the in vivo recombinant of step (e) of claim 11 with a third microorganism carrying a third plasmid, said third plasmid carrying a third selectable marker; and
   (g) selecting for *Vibrio cholerae* expressing the third selectable marker; and
   (h) curing the selecting product of step (g) of plasmids.

13. A method according to claim 12 wherein the first selectable marker and the second selectable marker are antibiotic resistance genes, and the third selectable marker is resistance to a heavy metal.

14. A method according to claim 13 wherein the first microorganism, the second microorganism, and the third microorganism are *E. coli* strains.

15. A method according to claim 11 wherein said deleted fragment of step (a) codes for *Vibrio cholerae* toxin or the A subunit thereof.

16. A method according to claim 11 wherein said flanking sequences of step (a) are about 7,000 base pairs on each side.

17. A method according to claim 11 wherein said first selectable marker and said second selectable marker are antibiotic resistant genes.

18. A method according to claim 12 wherein the first selectable marker in the in vivo recombinant of step (e) is inactivated by insertion of a third selectable marker in step (f).

19. A method according to claim 11 wherein said first plasmid is pJBK55.

20. A method according to claim 11 wherein said second plasmid is pR702.

21. A culture recovered from step (e) of the method of claim 11.

22. A culture recovered from step (g) of claim 12.

23. A culture of *Vibrio cholerae* comprising a *Vibrio cholerae* strain having a restriction endonuclease fragment of DNA coding for *Vibrio cholerae* toxin or the A subunit thereof deleted to confer avirulence and having the capacity to colonize the intestine of a host animal, said strain constructed by selection of an in vivo recombinant between virulent *Vibrio cholerae* N16961 of the Inaba serotype and a first plasmid, said first plasmid comprising *Vibrio cholerae* flanking sequences of the deleted DNA and a gene for a first selectable marker of foreign origin ligated to said flanking sequences to substitute for and to be in the place of said deleted DNA, said flanking sequences being of sufficient length to promote detectable in vivo recombination, said gene for said first selectable marker being incorporated into the chromosome of *Vibrio cholerae*, said selection being performed by selecting for said first selectable marker and for a second selectable marker to isolate an in vivo recombinant in the presence of a second plasmid carrying the second selectable marker, said second plasmid being incompatible with the first plasmid.

24. A culture of *Vibrio cholerae* according to claim 23 wherein said deleted DNA codes for the *Vibrio cholerae* toxins, or portion thereof.

25. A culture of *Vibrio cholerae* according to claim 23 wherein said sequences that flank the deleted DNA are about 7,000 base pairs on each side.

26. A culture of *Vibrio cholerae* according to claim 23 wherein said first selectable marker and said second selectable marker are resistance genes.

27. A culture of *Vibrio cholerae* comprising a *Vibrio cholerae* strain having a restriction endonuclease fragment of DNA coding for *Vibrio cholerae* toxin or the A subunit thereof deleted to confer a virulence and having the capacity to colonize the intestine of a host animal, said strain constructed by selection of in vivo recombinant JDK56 between a virulent *Vibrio cholerae* and a first plasmid, said first plasmid comprising *Vibrio cholerae* flanking sequences of the deleted DNA and a gene for a first selectable marker of foreign origin ligated to said flanking sequences to substitute for and to be in the place of said deleted DNA, said flanking sequences being of sufficient length to promote detectable in vivo recombination, said gene for said first selectable marker being incorporate into the chromosome of *Vibrio cholerae*, said selection being performed by selecting for said first selectable marker and for a second selectable marker to isolate in vivo recombinant JBK56 in the presence of a second plasmid carrying the second selectable marker, said second plasmid being incompatable with the first plasmid.

28. A culture of *Vibrio cholerae* according to claim 27 wherein said deleted DNA codes for the *Vibrio cholerae* toxins, or portion thereof.

29. A culture of *Vibrio cholerae* according to claim 27 wherein said sequences that flank the deleted DNA are about 7,000 base pairs on each side.

30. A culutre of *Vibrio cholerae* according to claim 27 wherein said first selectable marker and said second selectable marker are resistance genes.

31. A culture of *Vibrio cholerae* according to any of claims 23–26 wherein the first selectable marker of the in vivo recombinant is inactivated by insertion of a third selectable marker to yield a final strain of *Vibrio cholerae* JBK70.

32. A culture of *Vibrio cholerae* according to claim 31 wherein said final strain is JBK70 (PJBK51) and carries a plasmid expressing the B subunit of cholera toxin.

33. A method of isolating deletion mutants of *Vibrio cholerae* comprising the steps of
(a) constructing a first plasmid comprising *Vibrio cholerae* flanking sequences of a deleted restriction endonuclease fragment and a gene for a first selectable marker of foreign origin ligated to said flanking sequences to substitute for and to be in the place of said deleted fragment, wherein said flanking sequences are of sufficient length to promote detectable in vivo recombination; and
(b) mating a virulent strain of *Vibrio cholerae* with a first microorganism carrying the first plasmid; and
(c) selecting for *Vibrio cholerae* expressing the first selectable marker; and
(d) mating the selected product of step (c) with a second microorganism carrying a second plasmid with a second selectable marker, said second plasmid being incompatible with the first plasmid; and
(e) selecting for *Vibrio cholerae* expressing both the first selectable marker and the second selectable marker to isolate an in vivo recombinant; and
(f) mating the in vivo recombinant of step (e) with a third microorganism carrying a third plasmid, said third plasmid carrying a third selectable marker; and
(g) selecting for *Vibrio cholerae* expressing the third selectable marker wherein the selected product is JBK70; and
(h) curing the selected product of step (g) of plasmids.

34. A method of isolating deletion mutants of *Vibrio cholerae* comprising the steps of
(a) constructing a first plasmid comprising *Vibrio cholerae* flanking sequences of a deleted restriction endonuclease fragment and a gene for a first selectable marker of foreign origin ligated to said flanking sequences to substitute for and to be in the place of said deleted fragment, wherein said flanking sequences are of sufficient length to promote detectable in vivo recombination; and
(b) mating a virulent strain of *Vibrio cholerae* with a first microorganism carrying the first plasmid; and
(c) selecting for *Vibrio cholerae* expressing the first selectable marker; and
(d) mating the selected product of step (c) with a second microorganism carrying a second plasmid with a second selectable marker, said second plasmid being incompatible with the first plasmid; and
(e) selecting for *Vibrio cholerae* expressing both the first selectable marker and the second selectable marker to isolate an in vivo recombinant wherein the selected product is JBK56.

35. A method of isolating selection mutants of *Vibrio cholerae* comprising a the steps of
(a) constructing a first plasmid comprising *Vibrio cholerae* flanking sequences of one or more deleted restriction endonuclease fragments and a gene for a first selectable marker of foreign origin ligated to said flanking sequences to substitute for and to be in the place of said deleted fragment, wherein said sequences are of sufficient length to promote detectable in vivo recombination; and
(b) mating a virulent strain of *Vibrio cholerae* with a first microorganism carrying the first plasmid; and
(c) selecting for *Vibrio cholerae* expressing the first selectable marker; and
(d) mating the selected product of step (c) with a second microorganism carrying a second plasmid with a second selectable marker, said second plasmid being incompatible with the first plasmid; and
(e) selecting for *Vibrio cholerae* expressing both the first selectable marker and the second selectable marker to isolate an in vivo recombination wherein the selected product is JBK56; and
(f) mating the in vivo recombination of step (e) with a third microorganism carrying a third plasmid, said third plasmid carrying a third selectable marker; and
(g) selecting for *Vibrio cholerae* expressing the third selectable marker; and
(h) curing the selected product of step (g) of plasmids.

36. A culture of *Vibrio cholerae* comprising a *Vibrio cholerae* strain having a restriction endonuclease fragment of DNA coding for *Vibrio cholerae* toxin or the A subunit thereof deleted to confer avirulence and having the capacity of colonize the intestine of a host animal, said strain constructed by selection of an in vivo recombinant between a virulent *Vibrio cholerae* and a first plasmid, said first plasmid comprising *Vibrio cholerae* flanking sequences of the deleted DNA and a gene for a first selectable marker of foreign origin ligated to said flanking sequences to substitute for and to be in the place of said deleted DNA, said flanking sequences being of sufficient length to promote detectable in vivo recombination, said gene for said first selectable marker being incorporated into the chromosome of *Vibrio cholerae*, said selection being performed by selecting for said first selected marker and for a second selectable marker to isolate an in vivo recombinant in the presence of a second plasmid pR751 carrying the second selectable marker, said second plasmid pR751 being incompatible with the first plasmid.

37. A culture of *Vibrio cholerae* according to claim 36 wherein said deleted DNA codes for the *Vibrio cholerae* toxins, or portion thereof.

38. A culture of *Vibrio cholerae* according to claim 36 wherein said first selectable marker and said second selectable marker are resistance genes.

39. A method of isolating deletion mutants of *Vibrio cholerae* comprising the steps of
(a) constructing a first plasmid comprising *Vibrio cholerae* flanking sequences of a deleted restriction endonuclease fragment and a gene for a first selectable marker of foreign origin ligated to said flanking sequences to substitute for and to be in the place of said deleted fragment, wherein said flanking sequences are of sufficient length to promote detectable in vivo recombination; and
(b) mating virulent strain *Vibrio cholerae* N16961 of the Inaba serotype with a first microorganism carrying the first plasmid; and
(c) selecting for *Vibrio cholerae* the first selectable marker; and
(d) mating the selected product of step (c) with a second microorganism carrying a second plasmid with a second selectable marker, said second plasmid being incompatable with the first plasmid; and
(e) selecting for *Vibrio cholerae* expressing both the first selectable marker and the second selectable marker to isolate an in vivo recombinant.

40. The culture of *Vibrio cholerae* according to any one of claims 23, 25, or 26 wherein said first plasmid is pJBK55.

41. The culture of *Vibrio cholerae* according to any one of claims 23, 25, or 26 wherein said second plasmid is PR702.

42. The culture of *Vibrio cholerae* according to any one of claims 23 or 25 wherein the first selectable marker of the in vivo recombinant is inactivated by the insertion of a third selectable marker to yield a final strain of *Vibrio cholerae*.

43. The culture of *Vibrio cholerae* according to claim 26 wherein the first resistance gene of the in vivo recombinant is inactivated by the insertion of a third resistance gene to yield a final strain of *Vibrio cholerae*.

44. The culture of *Vibrio cholerae* according to claim 42 wherein said final strain carries a plasmid expressing the B subunit of cholera toxin.

45. The culture of *Vibrio cholerae* according to claim 43 wherein said final strain carries a plasmid expressing the B subunit of cholerae toxin.

46. A method of isolating deletion mutants of N16961 of the Inaba serotype of *Vibrio cholerae* comprising the steps of
  (a) constructing a first plasmid comprising *Vibrio cholerae* flanking sequences of a deleted restriction endonuclease fragment and a gene for a first selectable marker of foreign origin ligated to said flanking sequences to substitute for and to be in the place of said deleted fragment, wherein said flanking sequences are of sufficient length to promote detectable in vivo recombination;
  (b) mating N16961 of the Inaba serotype of *Vibrio cholerae* with a first microorganism carrying the first plasmid;
  (c) selecting a *Vibrio cholerae* expressing the first selectable marker;
  (d) mating the selected product of step (c) with a second microorganism carrying a second plasmid with a second selectable marker, said second plasmid being incompatable with the first plasmid; and
  (e) selecting for *Vibrio cholerae* expressing both the first selectable marker and the second selectable marker to isolate an in vivo recombinant.

47. A method according to claim 46 comprising the steps
  (f) mating the in vivo recombinant of step (e) with a third microorganism carrying a third plasmid, said third plasmid carrying a third selectable marker;
  (g) selecting for *Vibrio cholerae* expressing the third selectable marker; and
  (h) curing the selected product of step (g) of plasmids.

48. A method according to claim 47 wherein the first selectable marker and the second selectable marker are antibiotic resistance genes, and the third selectable marker is resistance to a heavy metal.

49. A method according to claim 47 wherein the first microorganism, the second microorganism, and the third microorganism are *E. coli* strains.

50. The culture of *Vibrio cholerae* according to claim 23 wherein said first plasmid is prepared by digesting plasmid JBK16 with ACC I restriction endonuclease, separating the ACC I fragments from the plasmid, ligating a gene for ampicillin resistance to the remaining DNA so that the ampicillin resistance gene is in the same location that the deleted toxin genes previously occupied, adding about 7,000 base pairs to each side of DNA sequences which flank the ampicillin resistance gene and cloning the resultant DNA into plasmid pRK 290 to form plasmid p JBK 55.

51. The culture of *Vibrio cholerae* according to claim 50 wherein said resultant DNA is cloned into an Eco RI site in said plasmid pRK290.

52. The culture of *Vibrio cholerae* according to claim 23 wherein said deleted DNA codes for the A subunit of *Vibrio cholerae* toxin to confer avirulence.

53. A method according to claim 46 wherein said deleted fragment of step (a) codes for *Vibrio cholerae* toxin or the A subunit thereof.

54. A method according to claim 46 wherein said flanking sequences of step (a) are about 7,000 base pairs on each side.

55. A method according to claim 46 wherein said first selectable marker and said second selectable marker are antibiotic resistant genes.

56. A method according to claim 47 wherein the first selectable marker in the in vivo recombinant of step (e) is inactivated by insertion of a third selectable marker in step (f).

57. A method according to claim 46 wherein said first plasmid is pJBK55.

58. A method according to claim 46 wherein said second plasmid is pR702.

59. A culture recovered from step (e) of the method of claim 46.

60. A culture recovered from step (g) of claim 47.

* * * * *